United States Patent [19]

Koch

[11] 4,024,128
[45] May 17, 1977

[54] BENZAZEPINYL SULFONYLUREAS AND INTERMEDIATES THEREFORE

[75] Inventor: Wolfgang Koch, Benken, Switzerland

[73] Assignee: Hoffmann-La Roche Inc., Nutley, N.J.

[22] Filed: Feb. 13, 1975

[21] Appl. No.: 549,572

[30] Foreign Application Priority Data

Feb. 22, 1974 Switzerland .................. 2539/74

[52] U.S. Cl. .................. 260/239 BB; 260/247.1 L; 260/293.59; 260/294.8 C; 260/309.6; 260/310 R; 260/326.37; 424/244; 424/272
[51] Int. Cl.² .................. C07D 223/16
[58] Field of Search .............. 260/326.37, 239 BB

[56] References Cited

UNITED STATES PATENTS

| 3,725,388 | 4/1973 | Greil et al. ............ 260/239 BB |
| 3,752,818 | 8/1973 | Plumpe et al. ............ 260/287 R |

FOREIGN PATENTS OR APPLICATIONS

| 749,742 | 4/1969 | Belgium ............ 260/239 BB |
| 1,443,911 | 12/1964 | Germany ............ 260/239 BB |
| 2,027,436 | 12/1971 | Germany ............ 260/239 BB |
| 1,933,388 | 1/1971 | Germany ............ 260/239 BB |

*Primary Examiner*—Donald G. Daus
*Assistant Examiner*—D. B. Springer
*Attorney, Agent, or Firm*—Samuel L. Welt; Bernard S. Leon; William G. Isgro

[57] ABSTRACT

Sulfonylurea derivatives of the formula

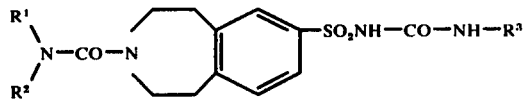

wherein $R^1$, $R^2$ and $R^3$ are as hereinafter set forth, are described. The sulfonylurea derivatives are useful as hypoglycemic agents.

15 Claims, No Drawings

BENZAZEPINYL SULFONYLUREAS AND INTERMEDIATES THEREFORE

BRIEF SUMMARY OF THE INVENTION

The invention relates to sulfonylurea derivatives of the formula

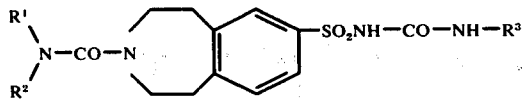

wherein $R^1$ is hydrogen, $C_1$–$C_6$-alkyl or $C_3$–$C_8$-cycloalkyl; $R^2$ is $C_1$–$C_6$-alkyl or $C_3$–$C_8$-cycloalkyl, or $R^1$ and $R^2$, taken together with the nitrogen atom to which they are attached are a heterocyclic ring; and $R^3$ is $C_1$–$C_8$-alkyl, $C_3$–$C_8$-alkenyl-alkyl, $C_5$–$C_8$-cycloalkyl, (2 or 3)-(cyclopenten or cyclohexen)-1-yl which may be substituted by $C_1$–$C_4$-alkyl, $C_1$–$C_4$-alkyl-$C_5$–$C_8$-cycloalkyl, $C_7$–$C_{10}$-endoalkylene-cycloalkyl, $C_3$–$C_8$-cycloalkyl-$C_1$–$C_4$-alkyl or $C_5$–$C_8$-cycloalkenyl-$C_1$–$C_4$-alkyl, or physiologically or pharmaceutically acceptable salts thereof.

In another aspect, the invention relates to novel intermediates.

DETAILED DESCRIPTION OF THE INVENTION

The sulfonylurea derivatives of the invention have the formula

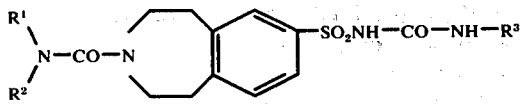

wherein $R^1$ is hydrogen, $C_1$–$C_6$-alkyl or $C_3$–$C_8$-cycloalkyl; $R^2$ is $C_1$–$C_6$ alkyl or $C_3$–$C_8$-cycloalkyl, or $R^1$ and $R^2$, taken together with the nitrogen atom to which they are attached, are a heterocyclic ring; and $R^3$ is $C_1$–$C_8$-alkyl, $C_3$–$C_8$-alkenyl-alkyl, $C_5$–$C_8$-cycloalkyl, (2 or 3)-(cyclopenten or cyclohexen)-1-yl, $C_1$–$C_4$-alkyl substituted (2 or 3)-(cyclopenten or cyclohexen)-1-yl, $C_1$–$C_4$-alkyl-$C_5$–$C_8$-cycloalkyl, $C_7$–$C_{10}$-endoalkylene-cycloalkyl, $C_3$–$C_8$-cycloalkyl-$C_1$–$C_4$-alkyl or $C_5$–$C_8$-cycloalkenyl-$C_1$–$C_4$-alkyl, and physiologically or pharmaceutically acceptable salts thereof.

Exemplary of alkyl are methyl, ethyl, propyl, isopropyl, butyl, or the like. Exemplary of cycloalkyl are cyclopentyl, cyclohexyl, cycloheptyl or the like. A heterocyclic ring formed by $R_1$ and $R_2$ and the nitrogen atom to which they are attached is, for example, a 3–6 membered ring such as pyrrolidine, piperidine, azetidine, aziridine, morpholine, or the like. Exemplary of alkenyl-alkyl are allyl, 2-butenyl or the like. Exemplary of an alkyl-cycloalkyl is 4-methyl-cyclohexyl or the like. Exemplary of cycloalkyl-alkyl are cyclohexyl-methyl, cyclopentylmethyl or the like. Exemplary of cycloalkenyl-alkyl are cyclohexenylmethyl or the like. Exemplary of endoalkylene-cycloalkyl are bornyl, norbornyl or the like.

The term "halogen" denotes all the halogens, i.e., bromine, chlorine, fluorine and iodine. The terms "alkoxy" and "alkylthio" denote an alkyl ether and an alkylthio ether group, respectively, in which the alkyl group is a straight or branched chain saturated hydrocarbon contaning 1 to 7 carbon atoms, for example, methoxy, methylthio, butoxy, butylthio, heptoxy, heptylthio, or the like. The term "acyl" denotes an aromatic hydrocarbon of 6 to 12 carbon atoms, for example, phenyl, tolyl or the like. the terms "aryloxy" and "arylthio" denote an aryl ether and an arylthio ethyl, respectively, in which the aryl group is as described above, for example, phenoxy, phenylthio, or the like.

In a preferred aspect, the invention comprises compounds of formula I wherein $R^1$ and $R^2$ are methyl or $R^1$ and $R^2$ together with the nitrogen atom to which they are attached are a heterocyclic ring, and $R^3$ is cyclohexyl, cyclopentyl or cyclopentylmethyl.

The sulfonylurea derivatives of formula I of the invention can be prepared by:

a. reacting a sulfonamide of the formula

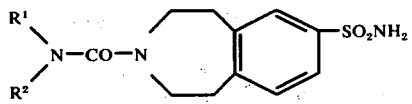

wherein $R^1$ and $R^2$ are as previously described or an alkali salt thereof, with an isocyanate of the formula

     R³NCO     III an azide of the formula

     R³CON₃     III-a or a carbamic acid derivative of the formula

     R³NHCOZ     IV wherein $R^3$ is as previously described and Z is halogen, alkoxy, aryloxy, alkylthio, arylthio, amino, —NHR³, arylamino, diarylamino, 1-imidazolyl, 3,5-dimethyl-1-pyrazolyl or trichloromethyl, or b. reacting a sulfonylisocyanate of the formula

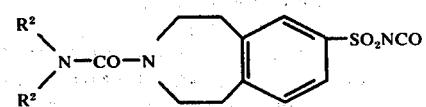

wherein $R^2$ is as previously described and wherein the two $R^2$ symbols are the same or different, or taken together with the nitrogen atom to which they are attached are a heterocyclic ring, or a sulfonylcarbamic acid derivative of the formula

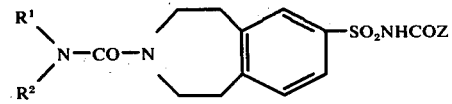

wherein $R^1$, $R^2$ and Z are as previously described, or both of $R^2$ taken together with the nitrogen atom to which they are attached are a heterocyclic ring, with an amine of the formula

     R³NH₂     VII or c. reacting a sulfonyl halide of the formula

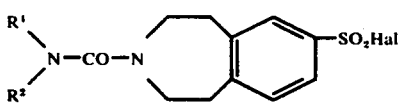

VIII wherein $R^1$ and $R^2$ are as previously described and Hal is halogen,
with a urea of the formula $R^3NHCONH_2$  IX wherein $R^3$ is as previously described,
or d. hydrolyzing a compound of the formula

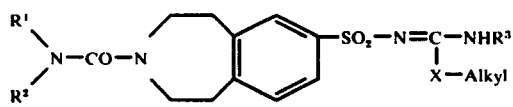

X or a compound of the formula

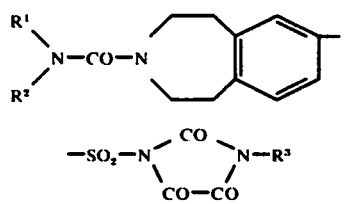

XI wherein $R^1$, $R^2$ and $R^3$ are as previously described and X is oxygen or sulfur,
or e. replacing the sulfur atom in the thiourea groupings of a thiourea derivative of the formula

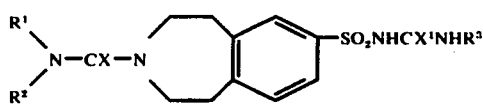

XII wherein $R^1$, $R^2$, $R^3$ and X are as previously described and $X^1$ is sulfur or oxygen with the proviso that X and $X^1$ are not simultaneously oxygen atoms,
with an oxygen atom, or f. oxidizing a sulfenylurea or sulfinylurea of the formula

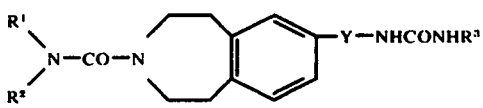

XIII wherein $R^1$, $R^2$ and $R^3$ are as previously described and Y is —S— or —SO—,
to the corresponding sulfonylurea, or g. reacting a sulfonylurea of the formula

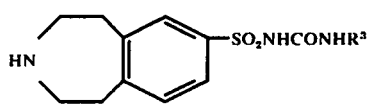

XIV wherein $R^3$ is as previously described, or a mineral acid salt thereof,
with an isocyanate of the formula $R^3NCO$  XV an azide of the formula $R^3CON_3$  XV-a or a carbamic acid derivative of the formula

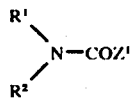

XVI wherein $R^1$ and $R^2$ are as previously described and $Z^1$ is halogen, alkoxy, aryloxy, alkylthio, arylthio, 1-imidazolyl, 3,5-dimethyl-1-pyrazolyl or trichloromethyl,
or h. reacting a sulfonylurea of the formula

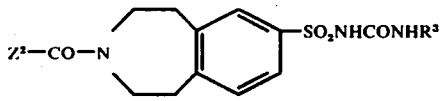

XVII wherein $R^3$ is as previously described and $Z^2$ is halogen, aryloxy, alkylthio, arylthio, 1-imidazolyl, 3,5-dimethyl-1-pyrazolyl or trichloromethyl,
with an amine of the formula

XVIII wherein $R^1$ and $R^2$ are as previously described,
or i. reacting a sulfinic acid of the formula

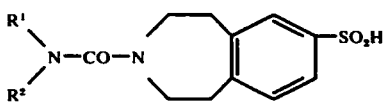

XIX wherein $R^1$ and $R^2$ are as previously described,
or a halide thereof with a hydroxyurea of the formula $R^3NHCONHOH$  XX wherein $R^3$ is as previously described,
or k. hydrolyzing a sulfonylcarbodiimide of the formula

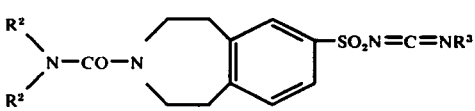

XXI or a chloroformic acid amidine of the formula

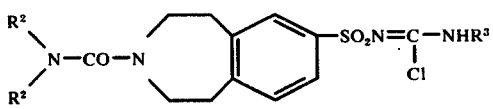

XXII wherein $R^2$ and $R^3$ are as previously described and wherein the two $R^2$ symbols are the same or different, or taken together with the nitrogen atom to which they are attached, are a heterocyclic ring, or l. reacting a sulfonylcarbamic acid derivative of the formula

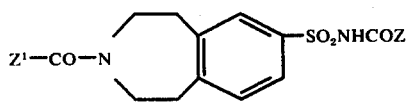

XXIII or a sulfonylisocyanate of the formula

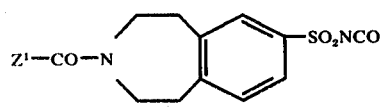

XXIV wherein Z and $Z^1$ are as previously described, with an amine of the formula

  $R^2NH_2$      XXV wherein $R^2$ is as previously described, or m. reacting 2,3,4,5-tetrahydro-1H-3-benzazepine-7-sulfonamide with an isocyanate of formula XV, an azide of formula XVa or a carbamic acid derivative of the formula

  $R^2NHCOZ^1$      XVIa wherein $R^2$ and $Z^1$ are as previously described.

The reaction according to process embodiments (a), (b), (c), (g), (h), (l) and (m) can be carried out in the presence or in the absence of a solvent. As the solvent there can be used an inert organic solvent, for example, a ketone such as acetone; an ether such as dioxane or tetrahydrofuran; or dimethylformamide. The temperature at which the reaction is carried out is not critical, However, a temperature in the range of from about 0° C. to about the boiling point of the solvent or the reaction mixture depending on the reactivity of the reactants. Conveniently, there can be added to the reaction mixture an inorganic base, for example, potassium carbonate, sodium hydroxide, or the like, or an organic base, for example, a sodium alcoholate, sodium hydride, diethylamine, pyridine, or the like. The reaction of process embodiment (c) is preferably carried out in the presence of a strong base such as sodium hydride.

The hydrolysis according to process embodiments (d) and (k) can be carried out using an acidic agent, for example, a mineral acid such as dilute hydrochloric acid; or an alkaline agent, for example, an alkali metal hydroxide or carbonate. Such hydrolysis is conveniently carried out in an inert water-miscible organic solvent.

The replacement of the sulfur atom by an oxygen atom in a thiourea grouping according to process embodiment (e) can be carried out, for example, by treating the starting material with a heavy metal salt or oxide, for example, lead, mercury or silver salts or oxides, or with a mild oxidizing agent, for example, hydrogen peroxide, nitric acid, or the like.

The oxidation of a sulfenylurea or sulfinylurea of formula XIII according to process embodiment (f) can be carried out utilizing an oxidizing agent such as hydrogen peroxide or a derivative thereof, for example, a peroxycarboxylic acid such as peracetic acid or utilizing a potassium permanganate, bromine or an alkali hypobromite. The oxidation can also be carried out in an electrolytic manner.

The reaction according to process embodiment (i) can be carried out in an inert solvent, for example, glacial acetic acid, dioxane, or the like, at a temperature in the range of from about room temperature to the boiling point of the solvent and in the presence of a condensing agent, for example, thionyl chloride, polyphosphoric acid, or the like.

The starting materials utilized in the present process, insofar as they are not known, can be prepared in a known manner or according to the processes described hereinafter.

The sulfonamides of formula II can be prepared by reacting 2,3,4,5-tetrahydro-1H-3-benzazepine-7-sulfonamide with an isocyanate of formula XV or a carbamic acid derivative of formula XVI. The sulfonylisocyanates of formula V can be prepared from the corresponding sulfonamides of formula II by reaction with phosgene. The sulfonylcarbamic acid derivatives of formula VI can be prepared by reacting the sulfonamides of formula II with a chloroformic acid ester or chlorothioformic acid ester to obtain compounds of formula VI, wherein Z is alkoxy, aryloxy, alkylthio or arylthio; with phosgene to obtain compounds of formula VI wherein Z is chlorine; with potassium cyanate, an alkyl- or arylisocyanate, or a N,N-disubstituted carbamoyl chloride to obtain compounds of formula VI, wherein Z is amino or substituted amino; with carbonyldiimidazole or carbonyl-di(3,5-dimethyl-1-pyrazole to obtain compounds of formula VI wherein Z is 1-imidazolyl or 3,5-dimethyl-1-pyrazolyl; or with trichloro-acetic acid methyl ester to obtain compounds of formula VI wherein Z is trichloromethyl. The sulfonyl chlorides of formula VIII can be prepared by first reacting 2,3,4,5-tetrahydro-1H-3-benzazepine with an isocyanate of formula XV or a carbamic acid derivative of formula XVI in a manner analogous to that described for the preparation of a sulfonamide of formula II and then treating the reaction product with chlorosulfonic acid. A sulfonyl chloride that is obtained can be converted into the corresponding sulfonyl fluoride with potassium fluoride. The sulfonyl bromides and iodides can be prepared by reacting the sulfonyl chloride with hydrazine and the hydrazide with bromine in chloroform or with iodine/potassium iodide/sodium acetate. The alkylation of the ureas of formula IX, for example, with dimethylsulfate, and reaction of the obtained pseudourea ether with a sulfonyl halide of formula VIII yields a compound of formula X wherein X is oxygen. The compounds of formula X wherein X is sulfur can be prepared by treating a sulfonamide of formula II in an aprotic solvent with an alkali hydroxide and carbon disulfide, methylating the product, for example, with dimethylsulfate, and reacting the obtained N-sulfonyliminodithiocarbonic acid dimethyl ester with an amine of the formula $R^3NH_2$.

Compounds of formula XI can be prepared by reacting a sulfonyl halide of formula VIII with a parabanic acid containing the group $R^3$. The substituted parabanic acid can be obtained by reacting a urea of formula IX with oxalyl chloride. The thiourea derivatives of formula XII wherein X is oxygen and $X^1$ is sulfur can be prepared by reacting a sulfonamide of formula II or the sodium salt thereof with an isothiocyanate of the formula $R^3NCS$. The thiourea derivatives of formula XII wherein X is sulfur and $X^1$ is oxygen or sulfur can be prepared by reacting 2,3,4,5-tetrahydro-1H-3-benzazepine-7-sulfonamide with a thiocarbamoyl chloride of the formula $(R^1, R^2)N$-CS-Cl and, thereafter, reacting the product obtained with an isocyanate of formula III to produce a desired thiourea derivative of formula XII wherein $X^1$ is oxygen or with a corresponding isothiocyanate to produce a desired thiourea derivative of formula XII wherein $X^1$ is sulfur.

The sulfenylureas and sulfinylureas of formula XIII can be prepared by the processes which follow: A sulfonyl chloride of formula VIII is reduced with zinc in an acidic solution to the corresponding thiophenol. Upon treatment with chlorine, the thiophenol yields a sulfenyl chloride from which, upon reaction with a urea of formula IX, there is obtained a sulfenylurea of formula XIII wherein Y is —S—. A sulfonyl chloride of formula VIII can be reduced by means of sodium sulfite to the corresponding sulfinic acid of formula XIX. The acid chloride obtained when the sulfinic acid of formula XIX is reacted with thionyl chloride yields, upon treatment with a urea of formula IX, a sulfinylurea of formula XIII wherein Y is —SO—. The sulfonylureas of formula XIV can be prepared by reacting 2,3,4,5-tetrahydro-1H-3-benzazepine-7-sulfonamide with an equimolar amount of chloroformic acid benzyl ester, reacting the product with an isocyanate of formula III and finally removing the carbobenzoxy group by catalytic hydrogenation. The sulfonylureas of formula XVII can be prepared by treating a sulfonylurea of formula XIV with a reactant such as phosgene, a chloroformic acid aryl ester, a chlorothioformic acid alkyl or aryl ester, carbonyldiimidazole, carbonyldi(3,5-dimethyl-1-pyrazole) or trichloroacetyl chloride. A thiourea derivative of formula XII wherein X is oxygen and $X^1$ is sulfur yields, upon treatment with phosgene in an inert solvent at room temperature, a chloroformic acid amidine of formula XXII and, at an elevated temperature, for example, at about 130° C., a sulfonylcarbodiimide of formula XXI. The sulfonylcarbamic acid derivatives of formula XXIII wherein Z is the same as $Z^1$ and the sulfonylisocyanates of formula XXIV wherein $Z^1$ is chlorine can be prepared by reacting 2,3,4,5-tetrahydro-1H-3-benzazepine-7-sulfonamide at least two equivalents of chloroformic acid ester, chlorothioformic acid ester, carbonyldiimidazole, carbonyldi(3,5-dimethyl-1-pyrazole), trichloroacetyl chloride or phosgene.

The sulfonylcarbamic acid derivatives of formula XXIII wherein Z and $Z^1$ are different and the sulfonylisocyanates of formula XXIV wherein $Z^1$ is other than chlorine can be prepared, for example, by first reacting 2,3,4,5-tetrahydro-1H-3-benzazepine-7-sulfonamide with an equivalent amount of chloroformic acid ester, chlorothioformic acid ester or trichloroacetyl chloride in order to introduce the $Z^1$—CO— group and subsequently reacting the product which is obtained in a manner analogous to that described earlier in connection with the preparation of sulfonylcarbamic acid derivatives of formula VI in order to introduce the group —CO—Z.

The compounds of formula I form physiologically or pharmaceutically acceptable salts with bases having non-toxic, pharmacologically acceptable cations. Suitable bases comprise, for example, alkali metal and alkaline earth metal hydroxides, carbonates or the like. Exemplary of such salts are the sodium and potassium salts. The variety of the salts of the invention is limited only by the criterion that the bases employed in forming the salts be non-toxic and physiologically or pharmaceutically acceptable.

The compounds of formula I have a strong blood sugar lowering activity, and are therefore useful as hypoglycemic agents, for example, in the treatment of diabetes. The blood sugar lowering activity of the compounds of formula I can be demonstrated in warm-blooded animals as described hereinafter: Female dogs fed with a standard diet are used in groups each comprising three animals for each test compound and dose to be tested. The animals are first fasted for 16 hours and then the test compound is administered per os in a gelatin capsule. Blood samples are taken before the administration of the test compound and at three 2-hour intervals, i.e., 2, 4 and 6 hours thereafter, heparinized and the glucose content of the plasma determined by means of the glucose-oxidase method [Anal. Biochem. 3, 131 (1962)] in a Technicon autoanalyzer. Four percent bovine albumin solution with a known glucose content is used as the standard. The results are obtained are evaluated statistically and the plasma glucose content is calculated as a percent of the original values. The results obtained with three compounds of formula I are given hereinafter in Table I.

Table I

| Test Results in the Dog | | | | |
|---|---|---|---|---|
| | | Plasma glucose as % of the original | | |
| Test Compound | Dosage p.o. ($\mu$ Mol/kg) | 2 hours | 4 hours | 6 hours |
| | | after administration | | |
| 1-Cyclohexyl-3-[(3-dimethylcarbamoyl-2,3,4,5-tetrahydro-1H-3-benzazepin-7-yl)sulfonyl]urea | 0.3 | 86% | 86% | 86% |
| | 1.0 | 69% | 74% | 86% |
| | 3.0 | 67% | 66% | 76% |
| 1-Cyclohexyl-3-{[2,3,4,5-tetrahydro-3-(1-pyrrolidinylcarbonyl)-1H-3-benzazepin-7-yl]sulfonyl}urea | 1.0 | 73% | 71% | 81% |
| 1-Cyclohexyl-3-[(3-ethylcarbamoyl-2,3,4,5-tetrahydro-1H-3-benzazepin-7-yl)sulfonyl]urea | 1.0 | 87% | 86% | 96% |

The tolerability by warm-blooded animals of the compounds of formula I is very good. Compounds of formula I have demonstrated a $DL_{50}$ in the mouse which is more than 5 g/kg. p.o. over a period of 24 hours.

The dosage at which the compounds of formula I can be utilized as hypoglycemic agents, for example, in the treatment of diabetes, can be in the range of from about 10 to about 100 mg. per day and depends on the requirements of the warm-blooded animal, as ascertained by the practitioner or on the particular compound to be administered.

The sulfonylurea derivatives of formula I provided by the invention can be used as medicaments, for example, in the form of pharmaceutical preparations which contain them in association with a compatible pharmaceutical carrier. Such as carrier can be an organic or inorganic inert carrier material suitable for enteral, percutaneus or parenteral administration, for example, water, gelatin, gum arabic, lactose, starch, magnesium stearate, talc, vegetable oils, polyalkyleneglycols, or the like. The pharmaceutical preparations can be made up in a solid form, for example, as tablets, dragees, suppositories or capsules, or in a liquid form, for example, as solutions, suspensions or emulsions. If desired, the pharmaceutical preparations may be sterilized and/or may contain adjuvants such as preserving, stabilizing, wetting or emulsifying agents, salts for variation of the osmotic pressure or buffers. They can also contain still other therapeutically active and valuable substances.

The following Examples further illustrate the present invention:

EXAMPLE 1

Preparation of
1cyclohexyl-3-[(3-dimethylcarbamoyl-2,3,4,5-tetrahydro-1H-3-benzazepin-7-yl)sulfonyl]urea 8.8 Ml. of 2N sodium hydroxide are added while stirring at 25° C. to a mixture of 5.2 g. of 3-dimethylcarbamoyl-2,3,4,5-tetrahydro-1H-3-benzazepine-7-sulfonamide in 180 ml. of acetone, during which the solid material first dissolves and then a new crystalline precipitate immediately results. 2.26 Ml. of cyclohexylisocyanate are then added thereto while cooling externally with ice and stirring, whereupon the solid material passes completely into solution and then a crystalline precipitate soon reappears. The mixture is subsequently stirred for 16 hours at 25° C., then diluted with 350 ml. of water, acidified to pH 2 with 3N hydrochloric acid and finally extracted twice with 500 ml. of chloroform each time. The chloroform extracts are dried over sodium sulfate and evaporated in vacuo at 60° C. The residue is dissolved in 25 ml. of acetone and crystallized by trituration. There is obtained 1-cyclohexyl-3-[(3-dimethylcarbamoyl-2,3,4,5-tetrahydro-1H-3-benzazepin-7-yl)sulfonyl]urea, m.p. 113° C. (with decomposition).

The starting material can be prepared as follows:

8.05 Ml. of dimethylcarbamoyl chloride are added dropwise while cooling at about 25° C. in the course of 3 minutes to a solution of 21.5 g. of 2,3,4,5-tetrahydro-1H-3-benzazepine-7-sulfonamide hydrochloride and 24.5 ml. of triethylamine in 400 ml. of methanol and the mixture is subsequently stirred for a further 15 hours, during which a crystalline precipitate results. By evaporation of the solvent in vacuo and digestion and washing of the crystalline evaporation residue with water, there is obtained 3-dimethylcarbamoyl-2,3,4,5-tetrahydro-1H-3-benzazepine-7-sulfonamide, m.p. 192°–193° C.

EXAMPLE 2

Preparation of
1-cyclohexyl-3-[(3-diethylcarbamoyl-2,3,4,5-tetrahydro-1H-3-benzazepine-7-yl)sulfonyl]urea In a manner analogous to that described in Example 1, from 3-diethylcarbamoyl-2,3,4,5-tetrahydro-1H-3-benzazepine-7-sulfonamide and cyclohexylisocyanate, there is obtained 1-cyclohexyl-3-[(3-diethylcarbamoyl-2,3,4,5-tetrahydro-1H-3-benzazepin-7-yl)sulfonyl]urea, m.p. 168°–169° C. The starting material can be prepared by the reaction of 2,3,4,5-tetrahydro-1H-3-benzazepine-7-sulfonamide hydrochloride with diethylcarbamoyl chloride in a manner analogous to that described in Example 1.

EXAMPLE 3

Preparation of
1-cyclohexyl-3-[(3-dipropylcarbamoyl-2,3,4,5-tetrahydro-1H-3-benzazepin-7-yl) sulfonyl]urea In a manner analogous to that described in Example 1, from 3-dipropylcarbamoyl-2,3,4,5-tetrahydro-1H-3-benzazepine-7-sulfonamide and cyclohexylisocyanate, there is obtained 1-cyclohexyl-3-[(3-dipropylcarbamoyl-2,3,4,5-tetrahydro-1H-3-benzazepin-7-yl)sulfonyl]urea, m.p. 179°–180° C. The starting material can be prepared by the reaction of 2,3,4,5-tetrahydro-1H-3-benzazepine-7-sulfonamide hydrochloride with dipropylcarbamoyl chloride in a manner analogous to that described in Example 1.

EXAMPLE 4

Preparation of
1-cyclohexyl-3-[(3-dibutylcarbamoyl-2,3,4,5-tetrahydro-1H-3-benzazepin-7-yl)sulfonyl]urea In a manner analogous to that described in Example 1, from 3-dibutylcarbamoyl-2,3,4,5-tetrahydro-1H-3-benzazepine-7-sulfonamide and cyclohexylisocyanate, there is obtained 1-cyclohexyl-3-[(3-dibutylcarbamoyl-2,3,4,5-tetrahydro-1H-3-benzazepin-7-yl)sulfonyl]urea, m.p. 118°–120° C. The starting material can be prepared by the reaction of 2,3,4,5-tetrahydro-1H-3-benzazepine-7-sulfonamide hydrochloride with dibutylcarbamoyl chloride in a manner analogous to that described in Example 1.

EXAMPLE 5

Preparation of
1-butyl-3-[(3-dimethylcarbamoyl-2,3,4,5-tetrahydro-1H-3-benzazepin-7-yl) sulfonyl]urea By the reaction of 3-dimethylcarbamoyl-2,3,4,5-tetrahydro-1H-3-benzazepine-7-sulfonamide with butylisocyanate in a manner analogous to that described in Example 1, there is obtained 1-butyl-3-[(3-dimethylcarbamoyl-2,3,4,5-tetrahydro-1H-3-benzazepin-7-yl) sulfonyl]urea, m.p. 93° C. (with decomposition).

EXAMPLE 6

Preparation of
1-cyclohexyl-3-{[2,3,4,5-tetrahydro-3-(1-pyrrolidinylcarbonyl)-1H-3-benzazepin-7-yl]sulfonyl}urea By the reaction of 2,3,4,5-tetrahydro-3-(1-pyrrolidinylcarbonyl)-1H-3-benzazepine-7-sulfonamide with cyclohexylisocyanate in a manner analogous to that described in Example 1, there is obtained 1- cyclohexyl-3-{[2,3,4,5-tetrahydro-3-(1-pyrrolidinyl-carbonyl)-1H-3-benzazepin-7-yl]sulfonyl}urea, m.p. 139°–141° C. The starting material can be prepared by the reaction of 2,3,4,5-tetrahydro-1H-3-benzazepine-7-sulfonamide hydrochloride with 1-pyrrolidinecarbonyl chloride in a manner analogous to that described in Example 1.

EXAMPLE 7

Preparation of
1-cyclohexyl-3-{[2,3,4,5-tetrahydro-3-(1-piperidinyl-carbonyl)-1H-3-benzazepin-7-yl]sulfonyl}urea By the reaction of 2,3,4,5-tetrahydro-3-(1-piperidinylcarbonyl)-1H-3-benzazepine-7-sulfonamide with cyclohexylisocyanate in a manner analogous to that described in Example 1, there is obtained 1-cyclohexyl-3-{[2,3,4,5-tetrahydro-3-(1-piperidinylcarbonyl)-1H-3-benzazepin-7-yl]sulfonyl}urea, m.p. 166°–167° C. The starting material can be prepared by the reaction of 2,3,4,5-tetrahydro-1H-3-benzazepine-7-sulfonamide hydrochloride with 1-piperidine-carbonyl chloride in a manneranalogous to that described in Example 1.

EXAMPLE 8

Preparation of
1-cyclohexyl-3-[(3-ethylcarbamoyl-2,3,4,5-tetrahydro-1H-3-benzazepin-7-yl)sulfonyl]urea By the reaction of 3-ethylcarbamoyl-2,3,4,5-tetrahydro-1H-3-benzazepine-7-sulfonamide with cyclohexylisocyanate in a manner analogous to that described in Example 1, there is obtained 1-cyclohexyl-3-[(3-ethylcarbamoyl-2,3,4,5-tetrahydro-1H-3-benzazepin-7-yl)sulfonyl]urea, m.p. 158°–160° C.

The starting material can be prepared in the following manner:

3.4 G. of 2,3,4,5-tetrahydro-1H-3-benzazepine-7-sulfonamide are dissolved in 50 ml. of dimethylformamide while warming at 60° C. and the solution is then rapidly cooled with an icebath. As soon as a temperature of 20° C. is reached, 1.18 ml. of ethylisocyanate are added dropwise while stirring, and the mixture is subsequently stirred at 25° C. for 0.5 hour. The solution is then concentrated in vacuo on a bath at 80° C. and the crystalline residue is digested with ether. There is obtained 3-ethylcarbamoyl-2,3,4,5-tetrahydro-1H-3-benzazepine-7-sulfonamide.

EXAMPLE 9

Preparation of
1-cyclohexyl-3-[(3-propylcarbamoyl-2,3,4,5-tetrahydro-1H-3-benzazepin-7-yl)sulfonyl]urea By the reaction of 3-propylcarbamoyl-2,3,4,5-tetrahydro-1H-3-benzazepine-7-sulfonamide with cyclohexylisocyanate in a manner analogous to that described in Example 1, there is obtained 1-cyclohexyl-3-[(3-propylcarbamoyl-2,3,4,5-tetrahydro-1H-3-benzazepin-7-yl)sulfonyl]urea. The starting material can be prepared by the reaction of 2,3,4,5-tetrahydro-1H-3-benzazepin-7-sulfonamide with propylisocyanate in a manner analogous to that described in Example 8.

EXAMPLE 10

Preparation of
1-cyclohexyl-3-[(3-butylcarbamoyl-2,3,4,5-tetrahydro-1H-3-benzazepin-7-yl)sulfonyl]urea By the reaction of 3-butylcarbamoyl-2,3,4,5-tetrahydro-1H-3-benzazepine-7-sulfonamide with cyclohexylisocyanate in a manner analogous to that described in Example 1, there is obtained 1-cyclohexyl-3-[(3-butylcarbamoyl-2,3,4,5-tetrahydro-1H-3-benzazepin-7-yl)sulfonyl]urea. The starting material can be prepared by the reaction of 2,3,4,5-tetrahydro-1H-3-benzazepine-7-sulfonamide with butylisocyanate in a manner analogous to that described in Example 8.

EXAMPLE 11

Preparation of
1-cyclohexyl-3-[(3-isopropylcarbamoyl-2,3,4,5-tetrahydro-1H-3-benzazepin-7-yl)sulfonyl]urea By the reaction of 3-isopropylcarbamoyl-2,3,4,5-tetrahydro-1H-3-benzazepine-7-sulfonamide with cyclohexylisocyanate in a manner analogous to that described in Example 1, there is obtained 1-cyclohexyl-3-[(3-isopropylcarbamoyl-2,3,4,5-tetrahydro-1H-3-benzazepin-7-yl)sulfonyl]urea. The starting material can be prepared by the reaction of 2,3,4,5-tetrahydro-1H-3-benzazepine-7-sulfonamide with isopropylisocyanate in a manner analogous to that described in Example 8.

EXAMPLE 12

Preparation of
1-cyclopentyl-3-[3-dimethylcarbamoyl-2,3,4,5-tetrahydro-1H-3-benzazepin-7-yl)sulfonyl]urea A solution of 8.0 g. of [(3-dimethylcarbamoyl-2,3,4,5-tetrahydro-1H-3-benzazepin-7-yl)sulfonyl]carbamic acid ethyl ester and 2.4 ml. of cyclopentylamine in 43 ml. of dioxane is heated under reflux for 1 hour and the solution subsequently evaporated in vacuo. Chromatography of the evaporation residue on 400 g. of silica gel with a mixture of 5 parts by volume of methanol and 95 parts by volume of chloroform yields the 1-cyclopentyl-3-[(3-dimethylcarbamoyl-2,3,4,5-tetrahydro-1H-3-benzazepin-7-yl)sulfonyl]urea, m.p. 179°–180° C.

The starting material can be prepared as follows:

A mixture of 7.5 g. of 3-dimethylcarbamoyl-2,3,4,5-tetrahydro-1H-3-benzazepine-7-sulfonamide, 13.9 g. of potassium carbonate, 9.6 ml. of chloroformic acid ethyl ester and 150 ml. of acetone is heated to reflux for 16 hours while stirring, then cooled to 25° C. and poured on to a mixture of 500 ml. of water and 1000 ml. of chloroform. The pH of the aqueous phase is then brought to 2.0 with 6N sulfuric acid while stirring. The chloroform phase is subsequently separated, dried over sodium sulfate and evaporated in vacuo. The evaporation residue is crystallized by the addition of ether. There is obtained [(3-dimethylcarbamoyl-2,3,4,5-tetrahydro-1H-3-benzazepin-7-yl)sulfonyl]carbamic acid ethyl ester of melting point 140°–141° C.

EXAMPLE 13

Preparation of
1-cyclopentylmethyl-3-[(3-dimethylcarbamoyl-2,3,4,5-tetrahydro-1H-3-benzazepin-7-yl)sulfonyl]urea By the reaction of [(3-dimethylcarbamoyl-2,3,4,5-tetrahydro-1H-3-benzazepin-7-yl)sulfonyl]carbamic acid ethyl ester with cyclopentylmethylamine in a manner analogous to that described in Example 12, there is obtained 1-cyclopentylmethyl-3-[(3-dimethylcarbamoyl-2,3,4,5-tetrahydro-1H-3-benzazepin-7-yl)-sulfonyl]urea, m.p. 165°–166° C.

EXAMPLE 14

Preparation of
1-[(3-ethylmethylcarbamoyl-2,3,4,5-tetrahydro-1H-3-benzazepin-7-yl)sulfonyl]-3-cyclohexylurea By the reaction of 3-ethylmethylcarbamoyl-2,3,4,5-tetrahydro-1H-3-benzazepine-7-sulfonamide with cyclohexylisocyanate in a manner analogous to that described in Example 1, there is obtained 1-[(3-ethylmethylcarbamoyl-2,3,4,5-tetrahydro-1H-3-benzazepin-7-yl)sulfonyl]-3-cyclohexylurea. The starting material can be prepared by first reacting ethylmethylamine with phosgene to give ethylmethylcarbamoyl chloride and subsequently bringing the latter to reaction with 2,3,4,5-tetrahydro-1H-3-benzazepine-7-sulfonamide hydrochloride.

EXAMPLE 15

Preparation of
1-cyclohexyl-3-{[3-[(hexahydro-1H-azepin-1-yl)carbonyl]-2,3,4,5-tetrahydro-1H-3-benzazepin-7-yl]sulfonyl} urea By the reaction of 3-[(hexahydro-1H-azepin-1-yl)carbonyl]-2,3,4,5-tetrahydro-1H-3-benzazepine-7-sulfonamide with cyclohexylisocyanate in a manner analogous to that described in Example 1, there is obtained 1-cyclohexyl-3-{[3-[(hexahydro-1H-azepin-1-yl)carbonyl]-2,3,4,5-tetrahydro-1H-3-benzazepin-7-yl]sulfnyl}urea, m.p. 155°–156° C. The starting material can be prepared by the reaction of 2,3,4,5-tetrahydro-1H-3-benzazepine-7-sulfonamide with hexahydro-1H-azepine-1-carbonyl chloride.

EXAMPLE 16

Preparation of
1-cyclohexyl-3-[(2,3,4,5-tetrahydro-3-morpholinocarbonyl-1H-3-benzazepin-7-yl)sulfonyl]urea By the reaction of 2,3,4,5-tetrahydro-3-morpholinocarbonyl-1H-3-benzazepine-7-sulfonamide with cyclohexylisocyanate in a manner analogous to that described in Example 1, there is obtained 1-cyclohexyl-3-[(2,3,4,5-tetrahydro-3-morpholinocarbonyl-1H-3-benzazepin-7-yl)sulfonyl]urea, m.p. 190°–191° C. The starting material can be prepared by the reaction of 2,3,4,5-tetrahydro-1H-3-benzazepine-7-sulfonamide with 4-morpholinecarbonyl chloride.

EXAMPLE 17

Preparation of
1-cyclohexyl-3-{[3-[3,6-dihydro-1(2H)-pyridinecarbonyl]-2,3,4,5-tetrahydro-1H-3-benzazepin-7-yl]sulfonyl} urea By the reaction of 3-[3,6-dihydro-1(2H)-pyridinecarbonyl]-2,3,4,5-tetrahydro-1H-3benzazepine-7-sulfonamide with cyclohexylisocyanate in a manner analogous to that described in Example 1, there is obtained 1-cyclohexyl-3-{[3-[3,6-dihydro-1(2H)-pyridinecarbonyl]-2,3,4,5-tetrahydro-1H-3-benzazepin-7-yl]-sulfonyl} urea, m.p. 173°–174° C. The starting material can be prepared by first reacting 1,2,3,6-tetrahydropyridine with phosgene and subsequently bringing the resulting 3,6-dihydro-1(2H)-pyridinecarbonyl chloride to reaction with 2,3,4,5-tetrahydro-1H-3-benzazepine-7-sulfonamide hydrochloride.

EXAMPLE 18

Preparation of
1-cyclohexyl-3-[(3-methylcarbamoyl-2,3,4,5-tetrahydro-1H-3-benzazepin-7-yl)sulfonyl]urea By the reaction of 3-methylcarbamoyl-2,3,4,5-tetrahydro-1H-3-benzazepine-7-sulfonamide with cyclohexylisocyanate in a manner analogous to that described in Example 1, there is obtained 1-cyclohexyl-3-[(3-methylcarbamoyl-2,3,4,5-tetrahydro-1H-3-benzazepin-7-yl)sulfonyl]urea. The starting material is prepared by the reaction of 2,3,4,5-tetrahydro-1H-3-benzazepine-7-sulfonamide with methylisocyanate in a manner analogous to that described in Example 8.

EXAMPLE 19

Preparation of
1-cycloheptyl-3-[(3-dimethylcarbamoyl-2,3,4,5-tetrahydro-1H-3-benzazepin-7-yl)sulfonyl]urea By the reaction of [(3-dimethylcarbamoyl-2,3,4,5-tetrahydro-1-H-3-benzazepin-7-yl)sulfonyl]carbamic acid ethyl ester with cycloheptylamine in a manner analogous to that described in Example 12, there is obtained 1-cycloheptyl-3-[(3-dimethylcarbamoyl-2,3,4,5-tetrahydro-1H-3-benzazepin-7-yl)sulfonyl]urea.

EXAMPLE 20

Preparation of
1-[(3-dimethylcarbamoyl-2,3,4,5-tetrahydro-1H-3-benzazepin-7-yl)sulfonyl]-3-(trans-4-methylcyclohexyl)urea By the reaction of [(3-dimethylcarbamoyl-2,3,4,5-tetrahydro-1H-3-benzazepin-7-yl)sulfonyl]carbamic acid ethyl ester with trans-4-methylcyclohexylamine in a manner analogous to that described in Example 12, there is obtained 1-[(3-dimethylcarbamoyl-2,3,4,5-tetrahydro-1H-3-benzazepin-7-yl)sulfonyl]-3-(trans-4-methylcyclohexyl)urea.

EXAMPLE 21

Preparation of
1-(3-cyclohexen-1-yl)-3-{[2,3,4,5-tetrahydro-3-(1-pyrrolidinylcarbonyl)-1H-3-benzazepin-7-yl]sulfonyl}urea By the reaction of 2,3,4,5-tetrahydro-3-(1-pyrrolidinylcarbonyl)-1H-3-benzazepin-7-sulfonamide and 3-cyclohexen-1-ylisocyanate in a manner analogous to that described in Example 1, there is obtained 1-(3-cyclohexen-1-yl)-3-{[2,3,4,5-tetrahydro-3-(1-pyrrolidinylcarbonyl)-1H-3-benzazepin-7-yl]sulfonyl}urea, m.p. 211°–212° C.

The following Example illustrates a typical pharmaceutical preparation containing one of the sulfonylurea derivatives provided by the present invention:

Example A

| | |
|---|---|
| 1-Cyclohexyl-3-{[2,3,4,5-tetrahydro-3-(1-pyrrolidinylcarbonyl)-1H-3-benzazepin-7-yl]sulfonyl}urea | 25.0 mg. |
| Lactose | 122.0 mg. |
| Maize Starch | 95.0 mg. |
| Talc | 7.2 mg. |
| Magnesium stearate | 0.8 mg. |
| Total | 250.0 mg. |

The 1-cyclohexyl-3-{[2,3,4,5-tetrahydro-3-(1-pyrrolidinylcarbonyl)-1H-3-benzazepin-7-yl]sulfonyl}urea and lactose are carefully mixed with a portion of the maize starch, granulated with a starch paste and dried. The dry, appropriately granulated mass is mixed with the residual maize starch, talc and magnesium stearate are added and the resulting mass is formed to tablets.

I claim:
1. A compound of the formula

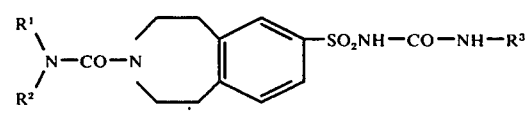

wherein $R^1$ is hydrogen, $C_1$–$C_6$-alkyl or $C_3$–$C_8$-cycloalkyl; $R^2$ is $C_1$–$C_6$-alkyl or $C_3$–$C_8$-cycloalkyl, or $R^1$ and $R^2$, taken together with the nitrogen atom to which they are attached, are a pyrrolidine ring; and $R^3$ is $C_1$–$C_8$-alkyl, $C_3$–$C_8$-alkenyl-alkyl, $C_5$–$C_8$-cycloalkyl, (2 or 3)-(cyclopenten or cyclohexen)-1-yl, $C_1$–$C_4$-alkyl substituted (2 or 3)-(cyclopenten or cyclohexen)-1-yl, $C_1$–$C_4$-alkyl-$C_5$–$C_8$-cycloalkyl, $C_7$–$C_{10}$-endoalkylene-cycloalkyl, $C_3$–$C_8$-cycloalkyl-$C_1$–$C_4$-alkyl or $C_5$–$C_8$-cycloalkenyl-$C_1$–$C_4$-alkyl, or physiologically or pharmaceutically acceptable salt thereof.

2. A compound in accordance with claim 1, wherein $R^1$ and $R^2$ are each methyl or taken together with the nitrogen atom to which they are attached, are a pyrrolidine ring, and $R^3$ is cyclohexyl, cyclopentyl or cyclopentylmethyl.

3. A compound of the formula

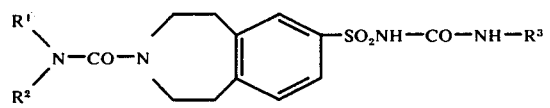

wherein $R^1$ and $R^2$, taken together with the nitrogen atom to which they are attached, are a pyrrolidine ring; and $R^3$ is $C_1$–$C_8$-alkyl, $C_3$–$C_8$-alkenyl-alkyl, $C_5$–$C_8$-cycloalkyl, (2 or 3)-(cyclopenten or cyclohexen)-1-yl, $C_1$–$C_4$-alkyl substituted (2 or 3)-(cyclopenten or cyclohexen)-1-yl, $C_1$–$C_4$-alkyl-$C_5$–$C_8$-cycloalkyl, $C_7$–$C_{10}$-endoalkylene-cycloalkyl, $C_3$–$C_8$-cycloalkyl-$C_1$–$C_4$-alkyl or $C_5$–$C_8$-cycloalkenyl-$C_1$–$C_4$-alkyl, or physiologically or pharmaceutically acceptable salts thereof.

4. A compound in accordance with claim 3, 1-cyclohexyl-3-{[2,3,4,5-tetrahydro-3-(1-pyrrolidinylcarbonyl)-1H-3-benzazepin-7-yl]sulfonyl}urea.

5. A compound in accordance with claim 3, 1-(3-cyclohexen-1-yl)-3-{[2,3,4,5-tetrahydro-3-(1-pyrrolidinylcarbonyl)-1H-3-benzazepin-7-yl]sulfonyl}urea.

6. A compound of the formula

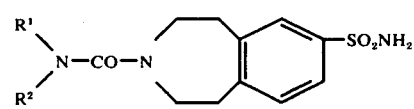

wherein $R^1$ is hydrogen, $C_1$–$C_6$-alkyl or $C_3$–$C_8$-cycloalkyl; $R^2$ is $C_1$–$C_6$-alkyl or $C_3$–$C_8$-cycloalkyl; or $R^1$ and $R^2$, taken together with the nitrogen atom to which they are attached, are a pyrrolidine ring.

7. A sulfonylisocyanate of the formula

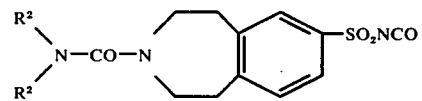

wherein $R^2$ is $C_1$–$C_6$-alkyl or $C_3$–$C_8$-cycloalkyl, or both of $R^2$ taken together with the nitrogen atom to which they are attached are a pyrrolidine ring.

8. A sulfonylcarbamic acid derivative of the formula

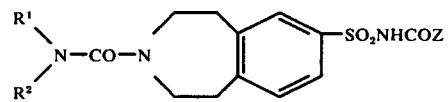

wherein $R^1$ is hydrogen, $C_1$–$C_6$-alkyl or $C_3$–$C_8$-cycloalkyl; $R^2$ is $C_1$–$C_6$-alkyl or $C_3$–$C_8$-cycloalkyl, or $R^1$ and $R^2$, taken together with the nitrogen atom to which they are attached, are a pyrrolidine ring; and Z is halogen, alkoxy of 1-7 carbon atoms, phenoxy, alkylthio of 1 to 7 carbon atoms, phenylthio, amino, phenylamino, diphenylamino, trichloromethyl, or —$NHR^3$ wherein $R^3$ is $C_1$–$C_8$-alkyl, $C_3$–$C_8$-alkenyl-alkyl, $C_5$–$C_8$-cycloalkyl, (2 or 3)-(cyclopenten or cyclohexen)-1-yl, $C_1$–$C_4$-alkyl-substituted (2 or 3)-(cyclopenten or cyclohexen)-1-yl, $C_1$–$C_4$-alkyl-$C_5$–$C_8$-cycloalkyl, $C_7$–$C_{10}$-endoalkylene-cycloalkyl or $C_3$–$C_8$-cycloalkenyl-$C_1$–$C_4$-alkyl.

9. A sulfonyl halide of the formula

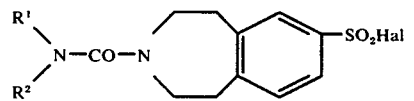

wherein $R^1$ is hydrogen, $C_1$–$C_6$-alkyl or $C_3C_8$-cycloalkyl; $R^2$ is $C_1$–$C_6$-alkyl or $C_3$–$C_8$-cycloalkyl, or $R^1$ and $R^2$, taken together with the nitrogen atom to which they are attached, are a pyrrolidine ring; and Hal is halogen.

10. A compound of the formula

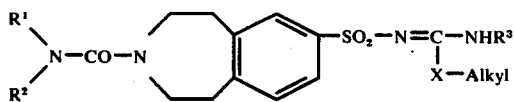 

wherein $R^1$ is hydrogen, $C_1$–$C_6$-alkyl or $C_3$–$C_8$-cycloalkyl; $R^2$ is $C_1$–$C_6$-alkyl or $C_3$–$C_8$-cycloalkyl, or $R^1$ and $R^2$, taken together with the nitrogen atom to which they are attached, are a pyrrolidine ring; and $R^3$ is $C_1$–$C_8$-alkyl, $C_3$–$C_8$-alkenyl-alkyl, $C_5$–$C_8$-cycloalkyl, (2 or 3)-(cyclopenten or cyclohexen)-1-yl, $C_1$–$C_4$-alkyl substituted (2 or 3)-(cyclopenten or cyclohexen)-1-yl, $C_1$–$C_4$-alkyl-$C_5$–$C_8$-cycloalkyl, $C_7$–$C_{10}$-endoalkylene-cycloalkyl, $C_3$–$C_8$-cycloalkyl-$C_1$–$C_4$-alkyl or $C_5$–$C_8$-cycloalkenyl-$C_1$–$C_4$-alkyl; and X is oxygen or sulfur.

11. A thiourea derivative of the formula

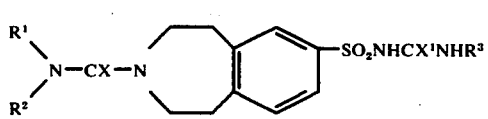

wherein $R^1$ is hydrogen, $C_1$–$C_6$-alkyl or $C_3$–$C_8$-cycloalkyl, $R^2$ is $C_1$–$C_6$-alkyl or $C_3$–$C_8$-cycloalkyl, or $R^1$ and $R^2$, taken together with the nitrogen atom to which they are attached, are a pyrrolidine ring; and $R^3$ is $C_1$–$C_8$-alkyl, $C_3$–$C_8$-alkenyl-alkyl, $C_5$–$C_8$-cycloalkyl, (2 or 3)-(cyclopenten or cyclohexen)-1-yl, $C_1$–$C_4$-alkyl substituted (2 or 3)-(cyclopenten or cyclohexen)-1-yl, $C_1$–$C_4$-alkyl-$C_5$–$C_8$-cycloalkyl, $C_7$–$C_{10}$-endoalkylene-cycloalkyl, $C_3$–$C_8$-cycloalkyl-$C_1$–$C_4$-alkyl or $C_5$–$C_8$-cycloalkenyl-$C_1$–$C_4$-alkyl; and X and $X^1$ each are oxygen or sulfur with the proviso that X and $X^1$ are not simultaneously oxygen atoms.

12. A sulfenylurea or sulfinylurea of the formula

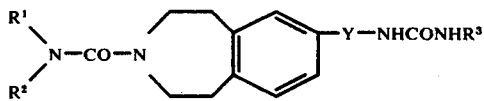

wherein $R^1$ is hydrogen, $C_1$–$C_6$-alkyl or $C_3$–$C_8$-cycloalkyl, $R^2$ is $C_1$–$C_6$-alkyl or $C_3$–$C_8$-cycloalkyl, or $R^1$ and $R^2$, taken together with the nitrogen atom to which they are attached, are a pyrrolidine ring; $R^3$ is $C_1$–$C_8$-alkyl, $C_3$–$C_8$-alkenylalkyl, $C_5$–$C_8$-cycloalkyl, (2 or 3)-(cyclopenten or cyclohexen)-1-yl, $C_1$–$C_4$-alkyl substituted (2 or 3)-(cyclopenten or cyclohexen)-1-yl, $C_1$–$C_4$-alkyl-$C_5$–$C_8$-cycloalkyl, $C_7$–$C_{10}$-endoalkylene-cycloalkyl, $C_3$–$C_8$-cycloalkyl-$C_1$–$C_4$-alkyl or $C_5$–$C_8$-cycloalkenyl-$C_1$–$C_4$-alkyl; and Y is —S— or —SO—.

13. A sulfinic acid of the formula

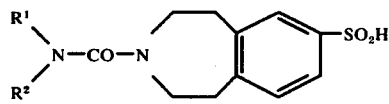

wherein $R^1$ is hydrogen, $C_1$–$C_6$-alkyl or $C_3$–$C_8$-cycloalkyl, $R^2$ is $C_1$–$C_6$-alkyl or $C_3$–$C_8$-cycloalkyl, or $R^1$ and $R^2$, taken together with the nitrogen atom to which they are attached, are a pyrrolidine ring.

14. A sulfonylcarbodiimide of the formula

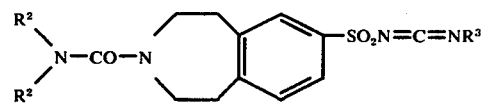

wherein $R^2$ is $C_1$–$C_6$-alkyl or $C_3$–$C_8$-cycloalkyl; $R^3$ is $C_1$–$C_8$-alkyl, $C_3$–$C_8$-alkenyl-alkyl or $C_5$–$C_8$-cycloalkyl, (2 or 3)-(cyclopenten or cyclohexen)-1-yl, $C_1$–$C_4$-alkyl substituted (2 or 3)-(cyclopenten or cyclohexen)-1-yl, $C_1$–$C_4$-alkyl-$C_5$–$C_8$-cycloalkyl, $C_7$–$C_{10}$-endoalkylene-cycloalkyl, $C_3$–$C_8$-cycloalkyl-$C_1$–$C_4$-alkyl or $C_5$–$C_8$-cycloalkenyl-$C_1$–$C_4$-alkyl; or both of $R^2$ taken together with the nitrogen atom to which they are attached, are pyrrolidine ring.

15. A chloroformic acid amidine of the formula

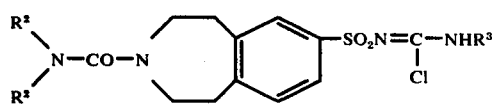

wherein $R^2$ is $C_1$–$C_6$-alkyl or $C_3$–$C_8$-cycloalkyl; $R^3$ is $C_1$–$C_8$-alkyl, $C_3$–$C_8$-alkenyl-alkyl, $C_5$–$C_8$-cycloalkyl, (2 or 3)-(cyclopenten or cyclohexen)-1-yl, $C_1$–$C_4$-alkyl substituted (2 or 3)-(cyclohepten or cyclohexen)-1-yl, $C_1$–$C_4$-alkyl-$C_5$–$C_8$-cycloalkyl, $C_7$–$C_{10}$-endoalkylene-cycloalkyl, $C_3$–$C_8$-cycloalkyl-$C_1$–$C_4$-alkyl or $C_5$–$C_8$-cycloalkenyl-$C_1$–$C_4$-alkyl, or both of $R^2$ taken together with the nitrogen atom to which they are attached, are a pyrrolidine ring.

* * * * *

UNITED STATES PATENT AND TRADEMARK OFFICE
CERTIFICATE OF CORRECTION

PATENT NO. : 4,024,128
DATED : May 17, 1977
INVENTOR(S) : Wolfgang Koch

It is certified that error appears in the above-identified patent and that said Letters Patent are hereby corrected as shown below:

Column 16, claim 9, line 63, "$C_3C_8$-cycloal-" should be:

$C_3$-$C_8$-cycloal-

Column 18, claim 14, line 33, "are pyrrolidine" should be:

are a pyrrolidine

Signed and Sealed this twenty-third Day of August 1977

[SEAL]

Attest:

RUTH C. MASON
Attesting Officer

C. MARSHALL DANN
Commissioner of Patents and Trademarks